United States Patent [19]

Barlow

[11] Patent Number: 4,632,105
[45] Date of Patent: Dec. 30, 1986

[54] HAND AND WRIST WRAP INCLUDING A THUMB LOOP

[75] Inventor: Carl S. Barlow, Sandpoint, Id.

[73] Assignee: Barlow, Inc., Sandpoint, Id.

[21] Appl. No.: 690,780

[22] Filed: Jan. 11, 1985

[51] Int. Cl.$^4$ .......................................... A61F 13/10
[52] U.S. Cl. ..................................... 128/165; 128/157
[58] Field of Search ................... 128/81 R, 81 A, 82, 128/80 R, 77, 80 D, 80 H, 153, 155, 157, 165, 166, 166.5, 169; 2/161 A, 162, 163, 170

[56] References Cited

U.S. PATENT DOCUMENTS

| | | | |
|---|---|---|---|
| 804,406 | 11/1905 | Hungad | 128/157 X |
| 1,899,092 | 2/1933 | Hogan | 128/81 R |
| 3,063,446 | 11/1962 | Levitt | 128/81 R |
| 3,556,091 | 1/1971 | Haig | 128/81 R |
| 3,777,751 | 12/1973 | Wise | 128/166 |
| 4,369,775 | 1/1983 | Gamm | 128/166 |
| 4,411,024 | 10/1983 | Hayes | 2/161 A X |

FOREIGN PATENT DOCUMENTS 9914 of 1890 United Kingdom ............. 128/81 R

Primary Examiner—Clifford D. Crowder
Attorney, Agent, or Firm—Wells, St. John & Roberts

[57] ABSTRACT

An elastic wrap includes a thumb loop section that facilitates application of the wrap by the wearer. The thumb loop is formed as an integrally with and at the end of an elongated elastic strap. The thumb loop is received over the wearer's thumb and is engaged about the thumb along the proximal phalanx between the distal and proximal knuckles. The thumb anchor loop is situated at an oblique angle to the remainder of the strap to facilitate positioning of the strap across the hand and wrist in such a manner to leave the palm or surface of the hand free when so desired. First and second fabric fastener members are provided along the length of the strap to facilitate selective application of the wrap around the wearer's hand, wrist, or forearm.

15 Claims, 10 Drawing Figures

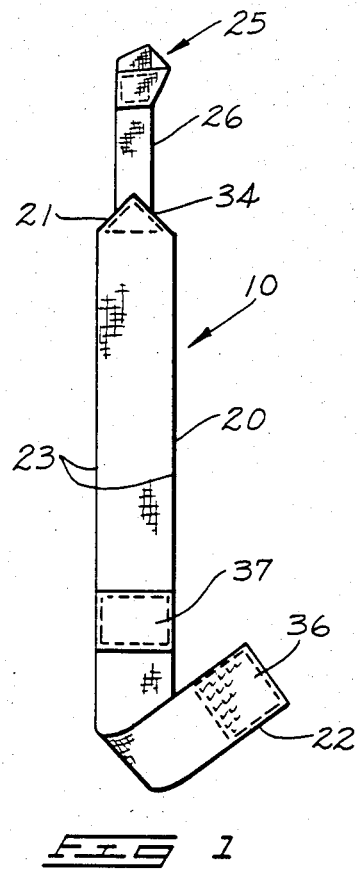
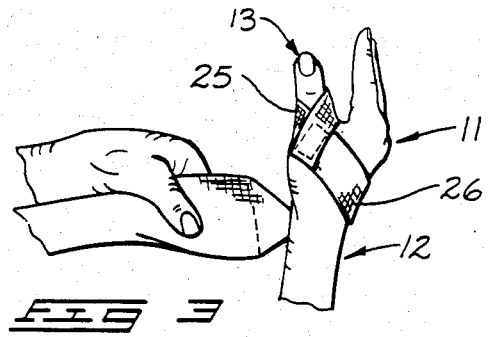
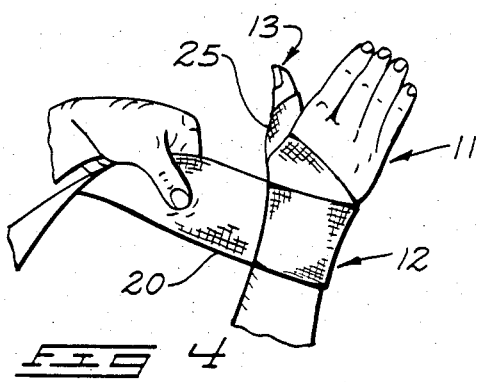
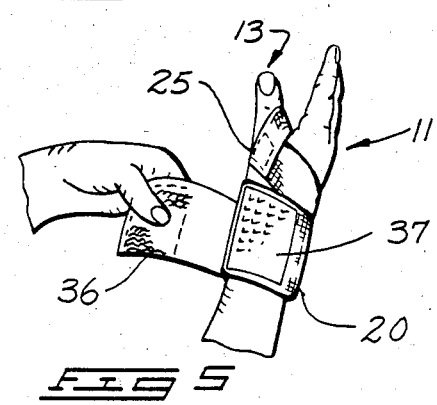
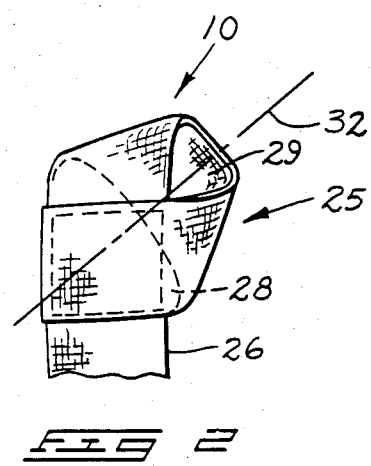
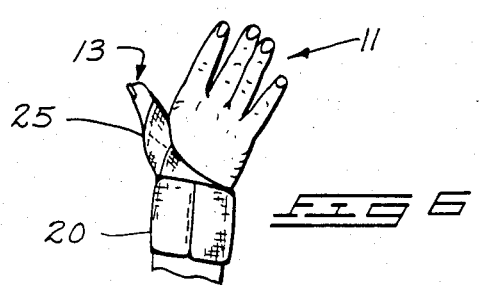

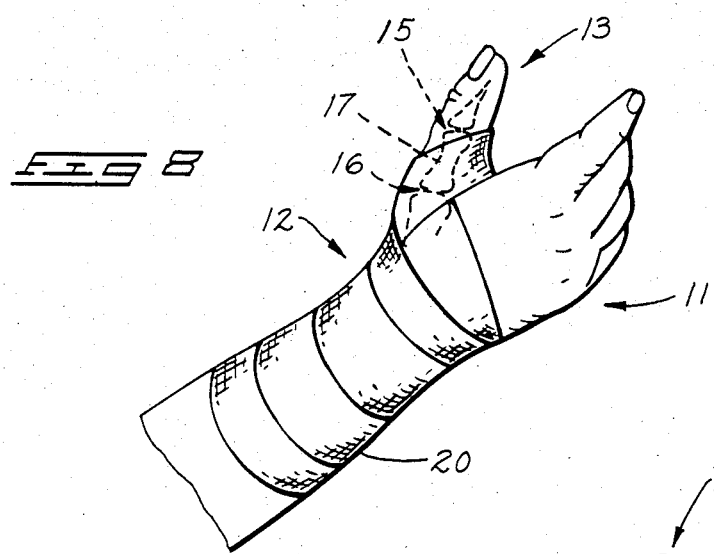
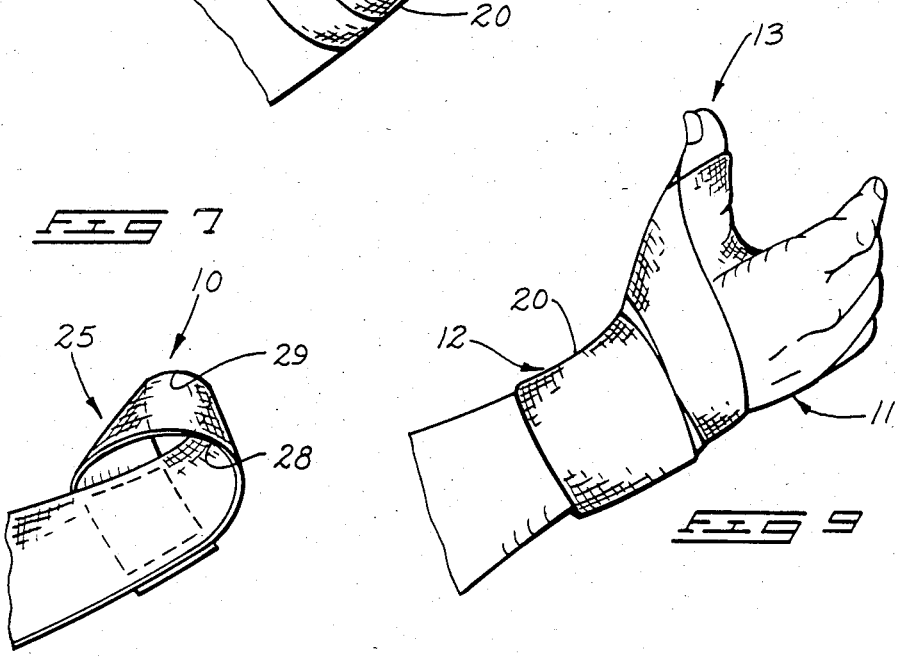
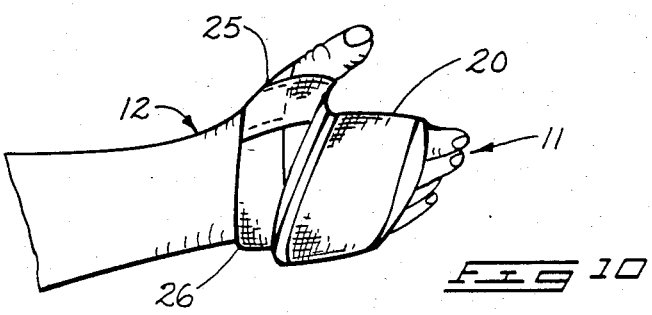

HAND AND WRIST WRAP INCLUDING A THUMB LOOP

FIELD OF THE INVENTION

The present invention relates to wrapping hands and wrists with elastic bandages to support and protect underlying tissues.

BACKGROUND OF THE INVENTION

Elastic bandages generally have to be placed on the hand or wrist by another individual. It is nearly impossible to place such bandages on one's own hand or wrist since both hands are required for the wrapping procedure. One hand is required to hold the free end of the elastic bandage in place while the other hand is used to wrap the bandage about the area being treated. This is particularly true where the hand or wrist being wrapped is injured or incapacitated.

Many individuals do not have help readily available. For example, many individuals such as the aged who are often alone could benefit by an effective wrist wrap to strengthen the hand and wrist to avoid injury during certain activities, for corrective therapy or for relief from discomfort in certain debilitating conditions such as arthritis.

Elastic wraps for the hand and wrist are also frequently used by athletes and others to guard against sprain and to reinforce otherwise weak joints during strenuous activities. Wrapping is sometimes done by trainers or fellow athletes. But instances do occur quite frequently where there is no one or no time available to assist with the lengthy wrapping procedures.

There is therefore a need for an elastic wrap that can be easily and quickly applied without the assistance of others.

Gloved or tubular wrist braces have been introduced in attempts to fill the above need. Examples of such are illustrated in U.S. Pat. Nos. 4,047,250; 3,533,407; and 3,710,790. These devices are commonly received over the hand or wrist and provide minimal capability for adjusting to size, tension, or the particular needs of the wearer. They function well only for the specific purposes envisioned in their design.

Other "wrap around" bandages have been introduced, differing from the glove or tube type by their elongated elastic structure. For example, U.S. Pat. No. 3,942,525 discloses an elastic wrap having a flange at one end that will facilitate gripping by the hand being wrapped. The structure is intended strictly for use in wrapping an area of the wrist.

U.S. Pat. No. 3,381,304 discloses a hand guard or grip including an elongated flexible strap with finger holes at opposed ends for attachment to specific fingers of the wearer's hand. The wrap functions strictly as a wear guard across the palm of the user.

U.S. Pat. No. 3,238,939 to Stubbs discloses a wrist support formed of a single elongated strap. The strap includes a thumb receiving recess which can be closed about the base of the wearer's thumb prior to a final wrapping about a specific area of the wrist. The thumb opening is used to locate the wrap in proper relation to the wearer's wrist.

U.S. Pat. No. 4,309,991 discloses a wrist brace making use of a glove or sleeve arrangement having thumb hole formed therein. The glove member is fixed to an elongated elastic wrap extending from an end attached to the glove at the wrist area to a free end. The elongated wrap can be wound about the wrist and hand area to secure a rigid brace member on the back surface of the glove in a specific position spanning the wearer's hand and wrist.

The above references all disclose various forms of braces and wraps directed to fairly specific applications. While some may offer the capability of being applied by the wearer, none until the present invention have provided the versatility needed to correct, protect, or relieve discomfort from various forms of disorders that can occur in the hand and wrist areas.

BRIEF DESCRIPTION OF THE DRAWINGS

The invention is illustrated in the accompanying drawings, in which:

FIG. 1 is a side view of the present elastic wrap with one end folded over;

FIG. 2 is an enlarged detail of a thumb anchor loop section of the present wrap;

FIGS. 3 through 6 are illustrative of a wrapping procedure for a wrist brace application of the present wrap;

FIG. 7 is a pictorial view of the thumb anchor detail shown in FIG. 2;

FIG. 8 is a pictorial view illustrating the present wrap applied along the wrist and forearm of the wearer;

FIG. 9 illustrates the present wrap used in a thumb brace application; and

FIG. 10 illustrates the present wrap applied across the fingers and adjacent knuckles.

DETAILED DESCRIPTION OF THE PREFERRED EMBODIMENT

In compliance with the constitutional purpose of the Patent Laws "to promote the progress of science and useful arts" (Article 1, Section 8), applicant submits the following disclosure of the invention.

FIG. 1 indicates an elongated elastic wrap embodying the principal features of the present invention. The elastic wrap is indicated in FIG. 1 by the numeral 10.

The elastic wrap 10 may be used and applied directly by the wearer to perform many different functions in bracing, protecting, correcting, or relieving discomfort in areas of the lower arm including the hand. FIGS. 3 through 6 and 8 through 10 exemplify various forms by which the present wrap can be attached and positioned in relation to the hand, wrist, and forearm areas. It should be understood though that the illustrations show only several of a nearly infinite variety of applications for the present wrap. The various applications shown are among the more popular known wrapping styles. However, the present wrap 10 can be applied by the individual in any manner or form that will produce a desired effect.

For purposes of this description, a very brief and basic anatomical discussion will be made with regard to the hand and wrist area. The hand (for purposes of this description) is labeled in the drawings by the reference numeral 11. The wrist is indicated at 12 and the thumb at 13. In FIG. 8 specific areas of the thumb significant to the following description are shown. They are the distal knuckle 15, the proximal knuckle 16, and the proximal phalanx 17 therebetween.

The present elastic wrap 10 as shown in FIG. 1 includes an elongated strap 20. It is preferred that the strap 20 be elastic along its full length from a first end 21 to a second end 22. It is also preferred that the strap include opposed side edges 23 extending between the ends 21 and 22.

An anchor or thumb loop 25 is formed along the elastic strap 20 at the first end 21. The thumb loop 25 may be shaped from an elastic section 26 of the strap having less width dimension (distance between edges 23) than the strap at the second end 22. In fact, the loop 25 may be formed of a second elastic strap secured or formed integrally as an extension of the strap 20. Regardless of its form of attachment, the section 26 is a part of the strap and extends from the enlarged width of the strap 20 to the anchor loop 25.

The thumb loop 25 is shown in substantial detail in FIGS. 2 and 7. It is is shaped as a hollow frustum to conform to the configuration of the thumb between the distal and proximal knuckles 15, 16. To this end, the frustum shaped loop includes an enlarged opening 28 to receive the proximal knuckle 16. A reduced opening 29 is situated at the opposite end of the frustum configuration to receive the distal knuckle 15.

The size of the openings 28 and 29 may vary with the hand size being used. It has been found, however, that a single size will function well with a wide variety of thumb sizes. It is preferred that the reduced opening have a diameter of approximately $\frac{3}{4}''$ and the enlarged opening, a diameter of approximately $1\frac{1}{2}''$. These dimensions, with the elasticity of the strap material, will accommodate all but extreme size variations. Size extremes can be accommodated by producing the present wrap in extra large and extra small sizes.

The width of the strap section at the loop is preferably substantially equal to the length of the proximal phalanx 17 of the thumb. This distance may vary from one hand to another. A width dimension for the elastic loop section 26 may correspondingly vary between $\frac{3}{4}''$ and $1\frac{3}{4}''$ wide. These figures represent extremes in size range. A preferred median size is approximately $1\frac{1}{4}''$ wide. The width is selected to assure a comfortable, full length engagement of the loop over the proximal phalanx of the thumb. By engaging the thumb only along the proximal phalanx, use of the thumb end extending beyond the loop is unimpaired.

The thumb loop 25 is formed along a central axis 32 that is preferably oblique to the overall length of the strap 20. This oblique angle is preferably an obtuse angle of approximately 135°. Such angular orientation of the thumb loop facilitates wrapping of the wrist and forearm area without the wrap interfering with the palmar surface of the hand. As indicated in FIG. 3, the strap can be attached with the elastic section 26 leading from the thumb loop across the back of the hand. The elastic section 26 extends diagonally across the back of the hand to the wrist where the wider portions of the strap 20 can be wrapped about the wrist and forearm in the manner shown in FIGS. 4 through 6 and 8.

The manner in which the thumb loop 25 is formed is simple yet very effective to facilitate individual wrapping and comfort. The loop is formed as a fold at the end of strap 20. The fold is made by folding the strap end back onto itself in the direction of the second strap end 22. The fold is made so the loop is formed at the desired oblique angle and so the free strap end can be attached, for example, by stitching 34 directly to the overlapped area of the strap. The double or overlapped areas reinforce the thumb loop and provide the advantage of padding the area adjacent to the proximal knuckle.

First and second fastener members 36 and 37 are provided along the length of the elastic strap 20. The first fastener member 36 is situated at the second strap end 22. The second fastener member 37 is situated along the strap length between the second end 22 and first end 21. Preferably, members 36 and 37 are situated on opposite flat surfaces of the strap 20. This facilitates connection when the wrap is complete as shown in FIG. 5. The fastener members 36, 37 are preferably formed of fabric "loop and hook" configurations that are commonly available on the marketplace and can be attached to the strap by sewing or appropriate adhesive. The distance between members 36 and 37 is sufficient to allow interconnection along the last wrap made. The members can be selectively overlapped along their lengths to vary the size or tension of the last wrap made.

Use of the present invention is made clear from the drawings and from the above description. It has already been indicated that uses for the present device are many and varied. Only a representative sampling is shown in the accompanying drawings. FIGS. 3 through 6, for example, show the procedure for attaching and wrapping one's hand to brace the wrist area. Firstly, the anchor loop 25 is received over the thumb with the narrow elastic section 26 loosely received over the back of the hand. The inherent angular orientation of the loop and strap is such that the strap will extend from the loop diagonally across the back of the hand toward the wrist. This positions the wider section of the strap at the wrist area as indicated in FIG. 3. Wrapping can conveniently begin as indicated in FIG. 4 and continue until the fastener members 36 and 37 can be comfortably engaged. The finished wrap is shown in FIG. 6.

It is noted that the palm of the hand in this configuration is completely free and that the entire wrapping procedure can be performed very easily by the wearer. Only one hand is required to complete the entire wrapping procedure.

FIG. 8 illustrates another arrangement in which the wearer has wrapped the wrist and forearm area to provide support and protection of possibly damaged tendons in the area. This particular wrap is also beneficial when loosely applied to relieve discomfort in the wrist and forearm area.

The wrap configuration shown in FIG. 9 is applied to brace and secure the thumb in position. This application can be used to hold the thumb securely following a dislocation or sprain and to protect the thumb against further damage during the healing process. The thumb loop is first secured about the thumb. The elastic section is then extended about the back of the hand and palm. The wider section of the elastic strap is then wound again about the thumb, wrapped about the hand and joined by the fastener members at the wrist to complete the application.

The particular application shown in FIG. 10 is frequently used to avoid damage to the knuckles of the fingers or to hold sprained fingers in position. Here, the thumb loop is secured as usual and the wrap is applied about the hand and finger areas. The body of the wrap is extended about the knuckles and fingers and is built up by overlapping the wrap on itself several times to add padding and protection of the finger and knuckle areas. This form is often used in heavy contact sports such as football.

Many other applications can be specially adapted by the wearer according to his or her own comfort. The thumb loop assures a firm anchor point for the first strap end. The angular orientation of the frustum configuration of the loop to the strap allows for variety in application and for substantial isolation of the wrap when used along the wrist and forearm. The palm of the associated hand can remain free along with the exposed part of the thumb to perform normal movements.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. An elastic wrap, comprising:
   an elongated elastic strap having a first end and a second end;
   an anchor loop at the first of said ends including a frustum shaped sleeve formed to be received about the proximal phalanx of a wearer's thumb and having a reduced opening for receiving the distal knuckle of the thumb and an enlarged opening to receive the proximal knuckle of the thumb;
   wherein the elastic strap includes a width dimension between opposed longitudinal sides and wherein the anchor loop is formed of an elastic section along the strap with a width dimension less than that of the strap and approximately equal to the length dimension of the proximal phalanx of the thumb;
   wherein the frustum shaped sleeve is formed along an axis oriented at an oblique angle to the strap such that when the thumb loop is placed over the thumb, the elastic strap is oriented to extend across the hand transverse to the fingers;
   a first fastener member at the second end of the strap; and
   a second fastener member along the elastic strap spaced toward the first strap end from the first fastener member.

2. The elastic wrap as claimed by claim 1 wherein the fastener members are hook and loop fabric fastener members and wherein the fastener members are situated on opposite side surfaces of the strap.

3. The elastic wrap as claimed by claim 1 wherein the enlarged opening of the anchor loop sleeve faces toward the elongated strap and the reduced opening faces away from the elongated strap.

4. The elastic wrap as claimed by claim 1 wherein the angle between the frustum axis and elastic strap is approximately 135°.

5. The elastic wrap as claimed by claim 1 wherein the anchor loop is formed by an end of the elongated elastic strap folded back on to itself to overlap the strap and fastened to the strap to form the frustum shaped open ended sleeve.

6. The elastic wrap as claimed by claim 1 wherein the width of the elastic strap section at the anchor loop is between $\frac{3}{4}"$ and $1\frac{3}{4}"$ wide.

7. The elastic wrap as claimed by claim 1 wherein the width of the elastic strap section at the anchor loop is approximately $1\frac{1}{4}"$.

8. The elastic wrap as claimed by claim 1 wherein the reduced opening faces away from the elastic strap and includes an approximate diameter of $\frac{3}{4}"$ and the enlarged opening faces toward the elastic strap and includes an approximate diameter of $1\frac{1}{2}"$.

9. An elastic hand and wrist wrap, comprising:
   an elongated elastic strap having side edges extending between opposed first and second ends and having a first width dimension;
   wherein the first end of the elastic strap includes a thumb loop formed of an elastic strap section having a width dimension less than said first width dimension, said thumb loop being in the form of a hollow frustum with one side edge of the strap defining a reduced opening at a reduced end of the frustum and the remaining side edge of the strap defining an enlarged opening at an enlarged end of the frustum, the loop being formed by an end of said section being folded back to overlap itself and fastened thereto to form the frustum along an axis at an oblique angle to the length of the elongated elastic strap;
   a first fastener member at the second end of the strap; and
   a second fastener member along the elastic strap spaced toward the first strap end from the first fastener member.

10. The elastic hand and wrist wrap as claimed by claim 9 wherein the central axis of the frustum is oriented at an oblique angle to the strap sides extending from the thumb loop to the second end.

11. The elastic hand and wrist wrap as claimed by claim 9 further comprising:
    a first fastener member adjacent the second strap end; and
    a second fastener member on the strap between second strap end and thumb loop for selective engagement with the first fastener member to selectively form a closed loop along the strap between the fastener members.

12. The elastic wrap as claimed by claim 9 wherein the angle between the frustum axis and elastic strap is approximately 135°.

13. The elastic wrap as claimed by claim 9 wherein the width of the elastic strap section at the thumb loop is between $\frac{3}{4}"$ and $1\frac{3}{4}"$ wide.

14. The elastic wrap as claimed by claim 9 wherein the width of the elastic strap section at the thumb loop is approximately $1\frac{1}{4}"$.

15. The elastic wrap as claimed by claim 9 wherein the reduced opening of the thumb loop faces away from the elastic strap and includes an approximate diameter of $\frac{3}{4}"$ and the enlarged opening faces toward the elastic strap and includes an approximate diameter of $1\frac{1}{2}"$.

* * * * *